United States Patent
Cherif-Cheikh

(10) Patent No.: US 6,544,545 B1
(45) Date of Patent: *Apr. 8, 2003

(54) NEEDLE-LESS PARENTERAL INTRODUCTION DEVICE

(75) Inventor: Roland Cherif-Cheikh, Moulineaux (FR)

(73) Assignee: Societe de Conseils de Recherches et d'Applications Scientifiques, S.A.S., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/658,911

(22) Filed: Sep. 11, 2000

Related U.S. Application Data

(63) Continuation of application No. 09/337,929, filed on Jun. 22, 1999, now Pat. No. 6,117,443, which is a continuation of application No. 08/793,955, filed on Mar. 12, 1997, now Pat. No. 6,120,786.

(51) Int. Cl.[7] ................................................. A61F 2/00
(52) U.S. Cl. ...................................... 424/426; 424/423
(58) Field of Search ................................. 424/423, 426

(56) References Cited

U.S. PATENT DOCUMENTS

| | | | |
|---|---|---|---|
| 2,589,388 A | 3/1952 | Hunter | 128/264 |
| 3,072,121 A * | 1/1963 | Feldmann | 604/192 |
| 3,572,335 A | 3/1971 | Robinson | 128/217 |
| 4,697,575 A | 10/1987 | Horowitz | 128/1.2 |
| 4,808,166 A | 2/1989 | Davidov | 604/114 |
| 4,820,267 A | 4/1989 | Harman | 604/60 |
| 4,871,094 A | 10/1989 | Gall et al. | 222/386 |
| 4,994,028 A | 2/1991 | Leonard et al. | 604/60 |
| 5,405,324 A | 4/1995 | Wiegerinck | 604/60 |
| 6,117,443 A * | 9/2000 | Cherif-Cheikh | 424/423 |
| 6,120,786 A * | 9/2000 | Cherif Cheikh | 424/423 |

FOREIGN PATENT DOCUMENTS

| | | |
|---|---|---|
| EP | 049 068 | 9/1981 |
| EP | 0 292 936 | 5/1988 |
| GB | 698275 | 1/1951 |
| GB | 2 091 554 | 4/1982 |
| NL | 8901124 | 12/1990 |
| WO | 93/23110 | 11/1993 |

* cited by examiner

Primary Examiner—Thurman K. Page
Assistant Examiner—Robert M. Joynes
(74) Attorney, Agent, or Firm—Fish & Richardson; Brian R. Morrill; Alan F. Feeney

(57) ABSTRACT

A needle-less device for the parenteral administration of a medicament is disclosed. The medicament has the shape of one end of a toothpick. It is placed in the bore of a barrel with the barrel having the shape of a nose cone at one end. A plunger is inserted into the other end of the bore. The plunger forces the medicament through the skin and into the subcutaneous layer of the patient without the need for penetration of the skin by a needle.

4 Claims, 4 Drawing Sheets

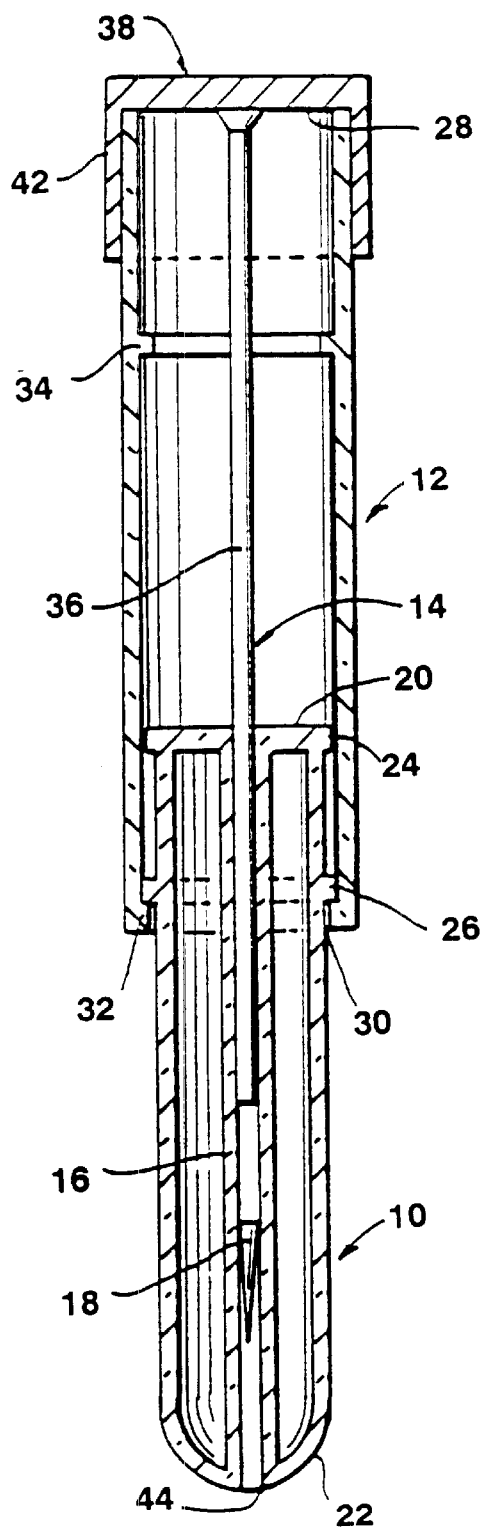
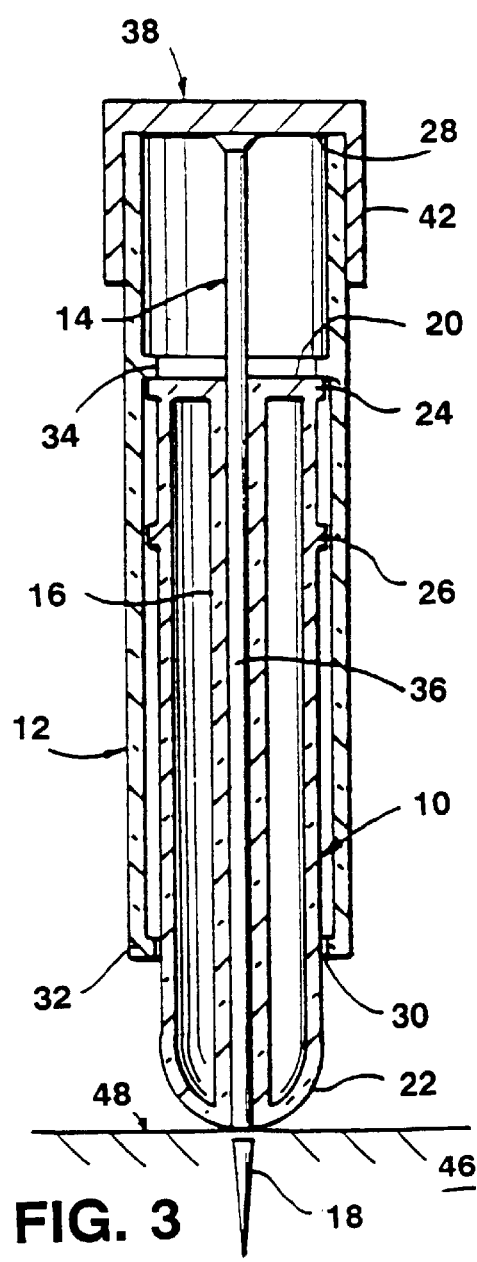
FIG. 2     FIG. 3

NEEDLE-LESS PARENTERAL INTRODUCTION DEVICE

CROSS-REFERENCE TO RELATED APPLICATIONS

This application is a continuation application of and claims priority to U.S. application Ser. No. 09/337,929, filed on Jun. 22, 1999 now U.S. Pat. No. 6,117,443; which is a continuation of U.S. application Ser. No. 08/793,955, filed on Mar. 12, 1997 now U.S. Pat. No. 6,120,786; which claims priority from PCT/IB95/00841, filed on Sep. 12, 1995; which claims priority from U.S. application Ser. No. 08/304,274, filed on Sep. 12, 1994, all of which are incorporated herein by reference in their entirety.

FIELD OF THE INVENTION

The present invention relates to parenteral introduction devices and, in particular, to a device for intramuscular or subcutaneous administration of a pharmaceutically active composition.

BACKGROUND OF THE INVENTION

The parenteral route is preferred over oral ones in many occurrences. For example, when the drug to be administered would partially or totally degrade in the gastrointestinal tract, parenteral administration is preferred. Similarly, where there is need for rapid responses in emergency cases, parenteral administration is usually preferred over oral.

Thus, while parenteral administration is desirable in many applications, as it is currently practiced, it presents substantial drawbacks. Probably the biggest drawback is the discomfort which it causes the patient to whom the drug is being administered. Parenteral preparations generally contain a large volume of liquid in which the drug is suspended or dissolved. Ratios of active ingredient to carrier commonly run from 1:100 to 1:1000. Especially where the active ingredient is poorly soluble or difficult to suspend, or when it has to be administered at high doses, or in both instances, a fairly large volume of liquid must be injected. The injection of the needle and the introduction of a fairly large volume of liquid cause parenteral administration to be more or less painful, and at least disagreeable, for most people. Furthermore, depending on its nature, the solvent or the suspending agent may itself be a cause of pain.

A further disadvantage to administration of drugs in a liquid carrier is that the drugs are frequently not stable in the liquid. Therefore, the liquid and drug must be mixed substantially contemporaneously with injection. This can be of substantial disadvantage where, for example, many hundreds of people must be treated over a course of days in order to stem an epidemic.

Accordingly, it would be interesting to find a mode of administration avoiding the use both of a needle and of a liquid solution or suspension.

Parenterally administered solid compositions for use in the controlled release of a medicament are known and devices allowing direct injection of a medicament without need of a liquid are known such as, for example, trocars for implants of rods or pellets, and the device shown in European Patent Application No. 0292936 A3 for injection of a solid. However, trocars and the device of European Patent Application No. 0292936 A3 still require use of a needle.

SUMMARY OF THE INVENTION

The applicant has now discovered a comparatively inexpensive device for the ready administration of solid or semi-solid drugs by the parenteral route. The applicant's device avoids completely the need for a needle. The solid drug is injected directly through the skin of a patient, e.g., a human or animal, by a plunger which enters the skin only to the degree necessary to position the solid drug. The medicament is suitably made in the shape of the end of a toothpick, i.e., it has a pointed end which gradually tapers to a cylindrical portion. The medicament has sufficient structural strength so that it can penetrate through the skin into the subcutaneous layer when it is administered with the parenteral introduction device of the present invention. Thus, the drug penetrates the skin and there is no need for the expense of discomfort of a needle to administer the drug parenterally. The present invention also includes an automatic device that can contain a number of doses of medicament which can be administered to a series of patients, one after the other.

Other features and advantages of the invention will be apparent from the drawings, detailed description, and from the claims.

BRIEF DESCRIPTION OF THE DRAWINGS

FIG. 2 shows the parenteral introduction device of the present invention in its retracted form;

FIG. 3 shows the device of the present invention with a medicament having been parenterally introduced into a patient;

DETAILED DESCRIPTION

Figure 1:
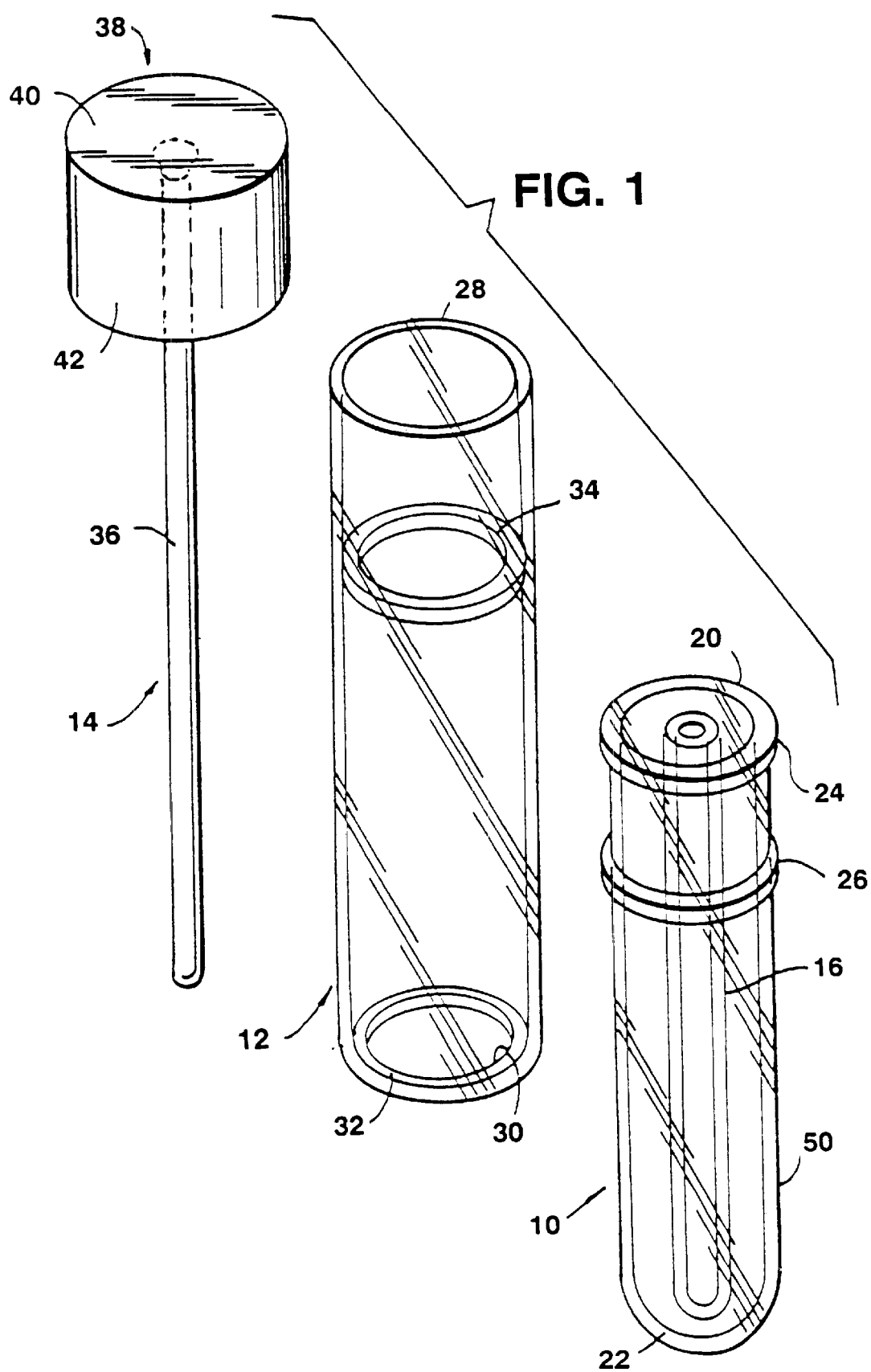
FIG. 1 is an exploded view of the parenteral introduction device according to the present invention.

Referring first to FIG. 1, which is an exploded view of the parenteral introduction device of the present invention, there are three essential elements, namely a main barrel 10, a sleeve member 12, and a plunger member 14. The main barrel 10 has central bore 16 which extends from one end 22 to the other end 20 of the main barrel 10. A medicament 18 (see FIG. 2) is carried in this central bore 16. The main barrel 10 includes protruding ring members 24 and 26 which act as stops as will be hereinafter discussed. The sleeve member 12 is open at both its top 28 and bottom 30 ends. The sleeve member 12 includes shoulders 32 and 34 to limit travel of the sleeve as hereinafter discussed. Plunger member 14 includes a plunger rod 36 and an end cap 38. The end cap 38 has a circular plate member 40 and a toroidally shaped flange 42. The plunger rod 36 has an external diameter at least a portion of which is substantially the same as, or slightly smaller than, the internal diameter of the bore 16.

FIG. 2 shows the parenteral introduction device of FIG. 1 in assembled condition and in a condition suitable for transport and storage. Plunger member 14 is press fit onto the end 28 of sleeve 12. Sleeve 12 has been forced over main barrel 10 so that shoulder 32 has passed over ring member 24 and has come to rest against ring member 26. The sleeve member is in sliding engagement with the exterior surface of the main barrel 10. Abutment of shoulder 32 with ring member 26 restrains the relative position of the sleeve 12 and the main barrel 10 so that the plunger 14 does not inadvertently dislodge the medicament 18 and push it through the said one end 22 of the main barrel 10. Ring member 24 prevents the unintentional separation of sleeve 12 from main barrel 10 since it will engage shoulder 32 before the sleeve 12 and the main barrel 10 are separated.

A seal 44 of biologically compatible material, such as cellulose or gelatin, may be applied to the end 22 of the main barrel 10 in order to maintain the sterility of the medicament 18 until the time it is administered. Alternatively, or additionally, the entire mechanism can be stored in a sterile environment such as a foil or cellophane pack (not shown).

Turning now to FIG. 3, there is shown the device in use. The said one end 22 of the main barrel 10 has been placed against the skin 48 of the patient to be treated, in such a way as to apply a tension on the zone where the medicament is to be injected. The plunger 14 and the sleeve 12, which travel together, have been urged down the main barrel 10 by applying pressure on the end cap 38 of plunger 14 until shoulder 34 comes into contact with the ring member 24. The plunger rod 36 has traversed the length of the bore 16 of the main barrel 10 and has pushed the medicament 18 through the skin 48 of the patient and into the subcutaneous layer 46. Shoulder 34 of sleeve 12 in combination with ring member 24 of main barrel 10 has limited the extent of travel of the plunger rod 36 in the main barrel 10. It is preferred that the rod 36 of plunger member 14 stop no more than 2 mm below the said one end 22 of the main barrel 10 and it is most preferred that the plunger member not extend at all beyond the said one end 22 of the main barrel 10.

Figure 4:
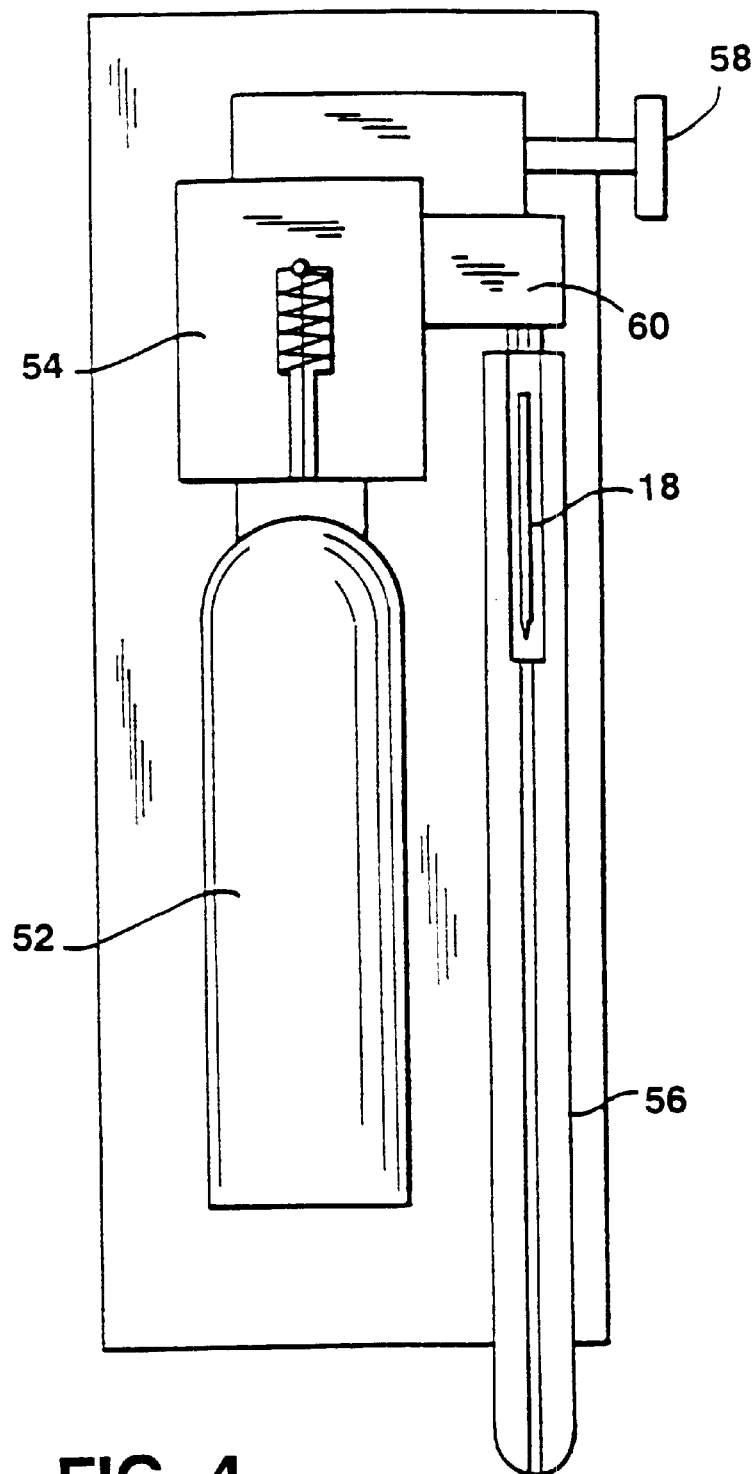
FIG. 4 shows the device of the invention with an automatic system where the plunger is replaced by a means for delivering pressurized gas.

In FIG. 4, there is shown an alternative embodiment of the present invention. In the alternative embodiment, the plunger 14 is replaced by a means for providing gas pressure from a reservoir 52 and through a valve 54. The medicament 18 travels through barrel 56 under pressure of the gas. Barrel 56 can be replaced for each new injection. When an injection is to be made, button 58 is depressed. This allows pressure to flow from reservoir 52 through valve 54 and regulator 60. The gas then forces the medicament 18 through the barrel 56 and into the patient (not shown). In the automatic device, this force is always the same because the amount of pressure exerted on the medicament is controlled by the regulator 60. Thus, the force of the injection is independent of any force applied by the operator.

Figure 5:
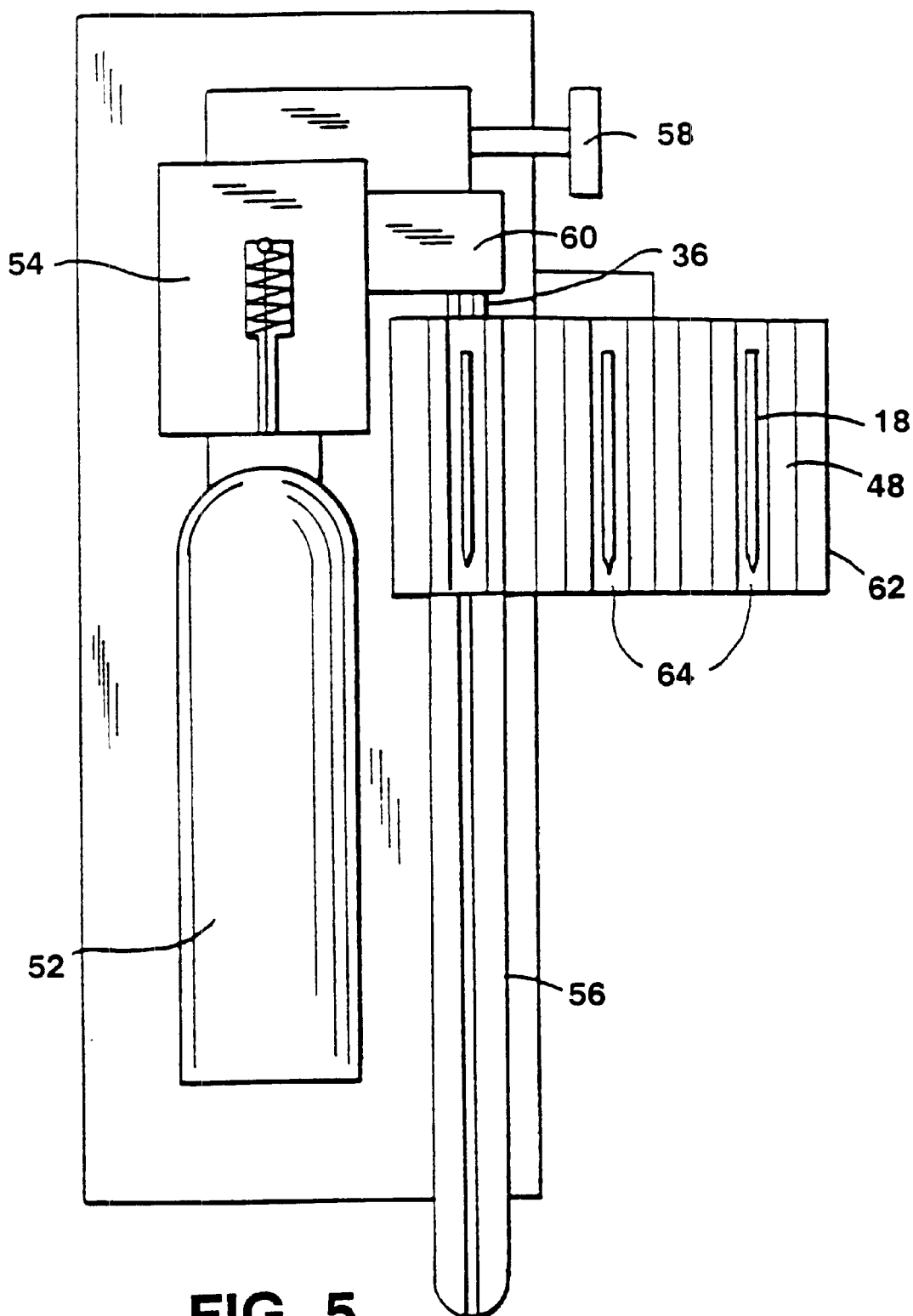
FIG. 5 shows an alternative embodiment of the automatic device for administering seriatim shots to a number of individuals.

In FIG. 5, there is disclosed an alternative embodiment of the automatic injector of FIG. 4. In this alternate embodiment, means are provided for injection of a plurality of doses to successive individuals using only a single injection device. This embodiment is illustrated in FIG. 5 where there is a magazine 62 which has a plurality of bores 64 with a medicament 18 fitted into each bore 64. As in the device of FIG. 4, gas pressure forces one of the medicaments 18 into a patient when button 58 is depressed. After delivery of the first medicament, the magazine 62 is moved to the left so that the next adjacent bore 64 and its associated medicament 18 are positioned above the barrel 56. The button 58 can be depressed to create a new gas pressure and to inject this next medicament 18 into the next patient, and thereafter, the rest of the medicaments 18 can similarly be administered seriatim to a series of individuals. Movement of the magazine can be effected manually or can be done automatically in a known manner.

All of the components of the device may suitably be made of plastic material, but it is preferred that the automatic device be made of metal, notably stainless steel. For the manual device, the plunger 36 can be made of metal, but it can also be made of plastic if its cross-section is increased sufficiently. Even where the plunger 36 is made of steel, it may be less expensive to make than the usual syringe since the device of the present invention does not require a stainless steel needle, the making of which requires quite a bit of precision. The main barrel 10 is preferably made with a nose cone shape at end 22. The main barrel can be made as a single piece, or, alternatively, the space between the outside wall 50 of the main barrel and wall of the central bore 16 can be hollow. The sleeve 12 is preferably made of transparent material so that the plunger rod 36 can be viewed therethrough, thus providing visual assurance that it is in its operative position.

The medicament 18 is preferably made of the shape of one end of a toothpick so that it can easily penetrate the skin and enter the subcutaneous layer. As is well known, one end of a toothpick has a point which tapers back to a cylindrical portion. The medicament is referred to as solid; however, it may be either solid or semi-solid so long as it has sufficient structural integrity to penetrate the skin without breaking apart. It has been found that a medicament having a crush strength of at least about 8 killipoise in the longitudinal direction is sufficiently strong, and lesser crush strengths are also usable, especially for administration to children, who have more tender skin than adults.

The amount of carrier in the medicament 18 depends on the drug and on the desired mode of action. As a general rule, the amount of active ingredient in the medicament is at least about 50%. With suitable medicaments which will have sufficient structural strength, the amount of medicament in the present invention can be up to 100%. The medicament may be prepared by conventional techniques such as compression, thermofusion, or extrusion. Compression suitably consists of a tabletting process in which a toothpick-shaped microtablet is formed. Thermofusion suitably consists of mixing and melting of the active ingredients and a carrier, if desired. The melted product is then molded into the toothpick-shaped medicament. Extrusion suitably consists of mixing the active ingredients and carrier, if desired, with a liquid to form a semisolid paste. The paste is then forced through a small diameter opening to form a rod. The needle-like tip can be formed prior to or after drying of the semisolid rods.

The size of the medicament 18 may be up to 2 mm in diameter but is preferably from about 0.2 to 0.8 mm, and most preferably from about 0.25 to 0.5 mm, in diameter for the cylindrical portion of the medicament, and about 1 mm to about 3 cm in length. The size will depend, of course, on the dose to be administered and the level of active ingredient present as compared to the amount of carrier.

The inside diameter of the bore 16 is preferably about 5–10% larger than the diameter of the medicament 18. This helps to ensure that the medicament does not get "hung up" or striated by minor imperfections, such as burrs, which may be introduced into the bore 16 during manufacture. At the same time, the diameter is limited to cause frictional engagement so that the medicament is less likely to be inadvertently dislodged from the bore prior to activation of the device. An oil can be added to the bore to increase the tendency of the medicament to remain in the bore; an oil will also assist in penetration through the skin.

The diameter of the medicament is not at all arbitrary; it has been found that the introduction of a pin with a diameter of about 2 mm or less is substantially painless. Such is not the case for larger diameters, and larger diameter medicaments may general only be administered via a trocar.

The active ingredient can be a peptide or a protein. Examples of such peptides include growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkaphalin, endothelin, calcitonin gene releasing peptide (CGRP), neuromedins, parathyroid hormone related protein (PTHrP), glucagon, neurotensin, adrenocorticotrophic hormone (ACTH), peptide YY (PYY), glucagon releasing peptide (GLP), factor VIII, vasoactive intestinal peptide (VIP), pituitary adenylated cyclass activating peptide (PACAP), motilin, substance P, neuropeptide Y (NPY), TSH, and analogs and fragments thereof. Other active ingredients include insulin, adrenaline, xylocaine, morphine, a glucocorticoid (e.g., dexamethasone), atropine, a cytostatic compound, estrogen, androgen, interleukins, digitoxin, biotin, testosterone, heparin, cyclosporin, penicillin, vitamins, antiplatelet activating factor agents (e.g., ginkgolides), or diazepam.

In order to provide instant delivery of the active ingredient, the carrier should be water soluble. Examples of water soluble carriers include hyaluronic acid, cellulose, e.g., hydroxypropylmethyl cellulose (HPMC), carboxymethyl cellulose (CMC), and hydroxyethyl cellulose (HEC), polyalcohols, e.g., mannitol, sugars, e.g., dextrose, mannose, and glucose, gelatin, polyvinylpyrrolidone, and starches. The carrier can also be water insoluble, but biodegradable to provide sustained delivery. Examples of suitable carriers include water insoluble polyesters of L-lactic acid, D-lactic acid, DL-lactic acid, L-lactide, D-lactide, DL-lactide, glycolide, glycolic acid, capralactone, and any optically active isomers, racemates, or copolymers thereof.

The following are illustrative examples of the parenteral administration of drugs in solid form as compared to the conventional liquid form, and are intended to show that the two means of administration have similar pharmaceutical efficacy.

EXAMPLE 1

A test was conducted with Insulin Human Recombinant (IHR) and Insulin Bovine Pancreas (IBP). IHR is pure water soluble insulin; IBP is zinc insulin, water insoluble and prepared usually using 16% glycerol. IHR and IBP represent about 26 Insulin Units (IU) per mg.

Different doses of insulin were compared with a conventional injectable formulation. In an in vivo test of hypoglycemic effect on rats, all these formulations were found as effective in terms of intensity and rapidity of action.

Insulin can be delivered as a dry solid and acts exactly like the usual parenteral formulation for bolus injection. The quantities needed with the device of the present invention are small enough to be administered in solid form as a 2 mm long cylinder with a 0.45 mm diameter. Patients can readily perform virtually painless introduction of solid insulin with the device of the present invention. This form of insulin is also stable for a longer time at room temperature and less expensive than the usual liquid form.

EXAMPLE 2

A formulation of a somatostatin analogue, D-Nal-cyclo [Cys-Tyr-D-Trp-Lys-Val-Cys]-Thr-$NH_2$ was made into injectable tablets by associating the dry material with gelatin and polyvinylpyrrolidone (PVP, 5–10%). The tablets were injected and compared to conventional solutions in terms of pharmacokinetic profiles. The methods gave substantially the same pharmacological results.

EXAMPLE 3

A synthetic anti-PAF, 4,7,8,10-tetrahydro-1-methyl-6-(2-chlorphenyl)-9-(4-methoxyphenyl-thiocarbamoyl)-pyrido-[4',3'-4,5] thieno [3,2-f]-1,2,4-triazolo [4,5-a] 1,4-diazepine, and a natural anti-PAF, ginkgolide B, were compared to conventional administration. The synthetic anti-PAF cannot conventionally be used parenterally because of its insolubility. Nevertheless, a very good correlation between pharmacological effect and blood concentration has been observed. Ginkgolide B is slightly soluble. For the same dose of product in solution form (pH 8.75), the effect was the same after initial injection but lasted only 2 hours with the solution whereas the effect lasted 24 hours with the solid dry formulation.

EXAMPLE 4

A prolonged formulation of decapeptyl (1 month) was made by a molding process with a molding machine into a shape of 0.8 mm diameter and some cm long.

Polylactidecoglycolide (PLGA, 80%) was used. The pharmacokinetically controlled delivery was equivalent to that of an implant or microspheres and the solid form was perfectly injectable subcutaneously or intravenously when the device was used in different species (rabbit, dog, rat, and pig).

Other Embodiments

It will be understood that the claims are intended to cover all changes and modifications of the preferred embodiments of the invention herein chosen for the purpose of illustration which do not constitute a departure from the spirit and scope of the invention.

What is claimed is:

1. A method of administering a medicament parenterally to a patient without the use of a needle, the method comprising:

providing a needle-less device comprising a barrel member and a plunger, the barrel member having first and second ends and a bore having an inside diameter for receipt of the medicament in solid form, the bore extending from the first end to the second end of the barrel, the plunger comprising an elongated rod having an outside diameter, the outside diameter being substantially the same as the inside diameter of the bore, the rod being inserted into the bore at the second end of the barrel, the plunger being capable of movement in the bore to push the medicament out the first end of the barrel member and through the skin of a patient when the barrel member is pressed against the skin of the patient, and the first end of the barrel member having a nosecone shape which precludes penetration of the skin by the barrel member, wherein the medicament is of sufficient structural strength to penetrate the skin of the patient;

contacting the first end of the barrel member to the patient's skin; and depressing the plunger, thereby forcing the medicament through the skin, to thereby administer the medicament to the patient.

2. The method of claim 1, wherein the diameter of the medicament is from about 0.2 to about 2 mm, the length of the medicament is from about 1 mm to about 5 cm, and the crush strength of the medicament is at least about 8 killipoise in the longitudinal direction.

3. The method of claim 1, wherein the diameter of the medicament is from about 0.2 to about 0.8 mm.

4. The method of claim 1, wherein the length of the medicament is from about 1 mm to about 3 cm.

* * * * *

UNITED STATES PATENT AND TRADEMARK OFFICE
CERTIFICATE OF CORRECTION

PATENT NO. : 6,544,545 B1
DATED : April 8, 2003
INVENTOR(S) : Roland Cherif-Cheikh It is certified that error appears in the above-identified patent and that said Letters Patent is hereby corrected as shown below:

Title page,
Item [63], Related U. S. Application Data, delete "Continuation of application No. 09/337,929, filed on Jun. 22, 1999, now Pat. No. 6,117,443, which is a continuation of application No. 08/793,955, Mar. 12, 1997, now Pat. No. 6,120,786." and insert
-- Continuation of application No. 09/337,929, filed on June 22, 1999, now Pat. No. 6,117,443, which is a continuation of application No. 08/793,955, filed on March 12, 1997, now Pat. No. 6,120,786, which is the national phase application of PCT/IB95/00841, filed on September 12, 1995, which is a continuation of 08/304,274, filed on September 12, 1994, now Pat. No. 5,542,920. --.

Signed and Sealed this

Twenty-first Day of March, 2006

JON W. DUDAS
*Director of the United States Patent and Trademark Office*